United States Patent [19]
Nakagawa et al.

[11] Patent Number: 5,968,474
[45] Date of Patent: *Oct. 19, 1999

[54] PURE PHASE TITANIUM-CONTAINING ZEOLITE HAVING MEL STRUCTURE, PROCESS FOR PREPARING SAME, AND OXIDATION PROCESSES USING SAME AS CATALYST

[75] Inventors: Yumi Nakagawa, Oakland; Chris Dartt, Pasadena, both of Calif.

[73] Assignee: Chevron U.S.A. Inc., San Francisco, Calif.

[*] Notice: This patent is subject to a terminal disclaimer.

[21] Appl. No.: 08/798,791

[22] Filed: Feb. 11, 1997

Related U.S. Application Data

[63] Continuation of application No. 08/434,466, May 4, 1995, abandoned, which is a continuation-in-part of application No. 08/316,010, Sep. 30, 1994, Pat. No. 5,645,812, which is a continuation-in-part of application No. 08/130,348, Oct. 1, 1994, abandoned.

[51] Int. Cl.[6] ............................. C01B 39/08; C01B 39/36
[52] U.S. Cl. ........................ 423/706; 423/713; 423/718; 423/DIG. 29; 502/77
[58] Field of Search .................................. 423/703, 705, 423/706, 713, 718, DIG. 29; 502/77

[56] References Cited

U.S. PATENT DOCUMENTS

| | | | |
|---|---|---|---|
| 4,391,785 | 7/1983 | Rosinski et al. | 423/706 |
| 4,410,501 | 10/1983 | Taramasso et al. | 423/705 |
| 4,519,998 | 5/1985 | Leen | 423/713 |
| 4,576,805 | 3/1986 | Chang et al. | 423/DIG. 29 |
| 4,666,692 | 5/1987 | Taramasso et al. | 502/77 |
| 4,707,345 | 11/1987 | Lok et al. | 502/77 |
| 4,833,260 | 5/1989 | Neri et al. | 549/531 |
| 5,160,717 | 11/1992 | Lok et al. | 502/77 |
| 5,374,747 | 12/1994 | Saxton et al. | 549/531 |
| 5,580,540 | 12/1996 | Nakagawa | 423/718 |
| 5,645,812 | 7/1997 | Nakagawa | 423/706 |

FOREIGN PATENT DOCUMENTS

| | | |
|---|---|---|
| 1001038A7 | 6/1989 | Belgium . |
| 0102097 | 3/1984 | European Pat. Off. . |
| 0190609 | 8/1986 | European Pat. Off. . |
| WO95/09812 | 4/1995 | WIPO . |

OTHER PUBLICATIONS

Reddy et al. "Crystallization Kinetics of a New Titanium Silicate with MEL Structure (TS–2)" *Zeolites,* Jan. 1992, vol. 12 p. 95.

Toby et al. "A High Resolution NMR & Synchrotron X–ray Diffraction Study of ZSM–11" *J. Mater Res.* vol. 3 No. 3 May/Jun. 1988 p. 563.

Reddy et al. "Synthesis, Characterization, & Catalytic Properties of Metallo–Titanium Silicate Molecular Sieves with MEL Topology" *J. Cat.* vol. 145 p. 73 (1994).

Jacobs et al. "Synthesis of High Silica Aluminosilicate Zeolites" pp. 147–166, 1987.

Clerici, *Applied Catalysis,* 68 (1991), Elsevier Science Publishers B.V., Amsterdam, pp. 249–261 (No Month).

Reddy et al., *Journal of Molecular Catalysis,* 70 (1991, Elsevier Sequoia, Lausanne, pp. 335–342 (No Month).

Reddy et al., *Journal of Catalysis 130,* (1991), pp. 440–446 (No Month).

Reddy et al., *Applied Catalysis,* 58 (1990), Elsevier Science Publishers B.V., Amsterdam, pp. L1–L4 (No Month).

*Primary Examiner*—Mark L. Bell
*Assistant Examiner*—David Sample
*Attorney, Agent, or Firm*—Richard J. Sheridan

[57] ABSTRACT

Titanium-containing zeolites containing the MEL crystal structure are prepared using an organic templating agent comprising 3,5-dimethylpiperidinium compounds. The zeolites can be made in the pure phase form, and are useful as catalysts for the oxidation of hydrocarbons.

10 Claims, No Drawings

PURE PHASE TITANIUM-CONTAINING ZEOLITE HAVING MEL STRUCTURE, PROCESS FOR PREPARING SAME, AND OXIDATION PROCESSES USING SAME AS CATALYST

CROSS REFERENCE TO RELATED APPLICATION

This is a continuation of application Ser. No. 08/434,466 now abandoned, filed May 4, 1995 which is a continuation-in-part of application Ser. No. 08/316,010, filed Sep. 30, 1994, now U.S. Pat. No. 5,645,812, which is a continuation-in-part of application Ser. No. 08/130,348, filed Oct. 1, 1994, now abandoned.

BACKGROUND OF THE INVENTION

1. Field of the Invention

The present invention relates to a titanium-containing zeolite having a framework structure designated MEL in pure phase form (referred to herein as "SSZ-46"), to a process for preparing crystalline titanium-containing zeolites having the MEL structure using an organic templating agent comprising at least one 3,5-dimethylpiperidinium (3,5-DMP) compound, and to oxidation processes using SSZ-46.

2. State of the Art

Titanium-containing zeolite ZSM-11 which contains the MEL framework structure (commonly referred to as "TS-2") and methods for making it are known. For example, Belgian Patent No. 1,001,038, issued Jun. 20, 1989, discloses the preparation of TS-2 using tetraalkylammonium cations, such as tetrabutylammonium hydroxide ("TBA"), as the organic templating agent. It does not, however, disclose the 3,5-DMP compounds of this invention as templating agents. Belgian Patent No. 1,001,038 is incorporated herein by reference in its entirety.

It has now been found that titanium-containing zeolites containing the MEL framework structure (e.g., TS-2) can be prepared using an organic template comprising at least one 3,5-DMP compound, that the zeolite can be made in pure phase form, and that this pure phase zeolite (SSZ-46) is useful as a catalyst in oxidation reactions.

SUMMARY OF THE INVENTION

The present invention provides a titanium-containing crystalline composition, as-synthesized and in the anhydrous state, whose general formula, in terms of mole ratios, is:

$YO_2/TiO_2 \quad >30$ $Q/YO_2 \quad 0.03-0.1$ wherein Q is an organic templating agent comprising at least one 3,5-dimethylpiperidinium compound, and Y is silicon, germanium, or mixtures thereof.

As used herein, the term "titanium-containing" refers to the fact that the zeolites of this invention contain titanium atoms in their framework structure.

In accordance with the present invention, there is also provided the titanium-containing zeolite SSZ-46 having no intergrowth within its crystalline structure of any crystalline structure other than the MEL structure. In particular, the SSZ-46 of this invention has no intergrowth of ZSM-5 (or its titanium-containing analog, TS-1) crystalline structure.

The present invention further provides the zeolite SSZ-46 having no intergrowth within its crystalline structure of any crystalline structure other than the MEL structure and having the X-ray diffraction pattern of Table I or Table II below.

In accordance with the present invention, there is also provided a process for preparing titanium-containing zeolites containing the MEL crystal structure which comprises:

(a) preparing an aqueous solution containing (1) sources of titanium oxide; (2) sources of an oxide selected from oxides of silicon, germanium or mixtures thereof; and (3) an organic templating agent comprising at least one 3,5-dimethylpiperidinium compound;

(b) maintaining the aqueous solution under conditions sufficient to form crystals of said titanium-containing zeolite; and (c) recovering the crystals of said titanium-containing zeolite.

The present invention also provides the above-described process for preparing titanium-containing zeolites wherein the organic templating agent comprises a mixture of a 3,5-dimethylpipperidinium compound and a tetraalkylammonium compound.

Further provided in accordance with this invention are the above-described processes for preparing titanium-containing zeolites wherein the zeolite so prepared is in pure phase form (i.e., is SSZ-46).

The present invention further provides a process for oxidation of hydrocarbons comprising contacting said hydrocarbon with hydrogen peroxide in the presence of a catalytically effective amount of a crystalline, titanium-containing molecular sieve for a time and at a temperature effective to oxidize said hydrocarbon, wherein the crystalline titanium-containing molecular sieve is a zeolite whose general formula is, after calcination, $$TiO_2:wSiO_2$$

where w>30, and which has the X-ray diffraction lines of Table II below (i.e., the zeolite is SSZ-46).

The present invention also provides a process for epoxidation of an olefin comprising contacting said olefin with hydrogen peroxide in the presence of a catalytically effective amount of a crystalline, titanium-containing molecular sieve for a time and at a temperature effective to epoxidize said olefin, wherein the crystalline titanium-containing molecular sieve is a zeolite whose general formula is, after calcination, $$TiO_2:wSiO_2$$

where w>30, and which has the X-ray diffraction lines of Table II below.

Further provided in accordance with this invention is a process for oxidizing cyclohexane comprising contacting said cyclohexane with hydrogen peroxide in the presence of a catalytically effective amount of a crystalline, titanium-containing molecular sieve for a time and at a temperature effective to oxidize said cyclohexane, wherein the crystalline titanium-containing molecular sieve is a zeolite whose general formula is, after calcination, $$TiO_2:wSiO_2$$

where w>30, and which has the X-ray diffraction lines of Table II below.

Among other factors, the present invention is based on the discovery that titanium-containing zeolites containing the MEL crystal structure can be made using an organic templating agent comprising at least one 3,5-dimethylpiperidinium compound. It is especially surprising that, by using these 3,5-dimethylpiperidinium compounds as the templating agent, the titanium-containing zeolite can be prepared in essentially pure phase form. Heretofore, it has been difficult to prepare titanium-containing the MEL crystal structure (such as TS-2) using conventional templating agents without also crystallizing the closely related zeolite ZSM-5.

DETAILED DESCRIPTION OF PREFERRED EMBODIMENTS

In one embodiment the present invention comprises:

(a) preparing an aqueous solution comprising sources of oxides capable of forming titanium-containing zeolites containing the MEL crystal structure and an organic templating agent comprising at least one 3,5-dimethylpiperidinium compound;

(b) maintaining the aqueous solution under conditions sufficient to form crystals of said titanium-containing zeolite; and (c) recovering the crystals of said titanium-containing zeolite.

The Templating Agent

The templating agents useful in the present process are water-soluble 3,5-dimethylpiperidinium compounds which are capable of acting as a templating agent to form titanium-containing zeolites containing the MEL crystal structure.

They have a molecular structure of the general form:

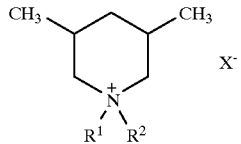

wherein $R^1$ and $R^2$ independently represent an alkyl group, either branched or unbranched, substituted or unsubstituted, containing from 1 to about 7 carbon atoms. In addition, $R^1$ and $R^2$ together may comprise a cyclic alkyl ring system, which, including the positively charged nitrogen atom, contains from 4 to 7 atoms, said ring system being unsubstituted or substituted with branched or unbranched alkyl groups having, e.g., one to three carbon atoms. $X^-$ is an anion which is not detrimental to the formation of the titanium-containing zeolite, such as those described below. Preferred 3,5-DMP compounds are 3,5-dimethyl-N,N-diethylpiperdinium compounds; 3,5-dimethyl-N-methyl-N-ethylpiperidinium compounds; and spiro 3,5-dimethylpiperidinium compounds such as 1-azonia-3,5,7-trimethyl-spiro[5.4] decane compounds.

The anion for the salt may be essentially any anion such as halide or hydroxide which is not detrimental to the formation of the zeolite. As used herein, "halide" refers to the halogen anions, particularly fluorine, chlorine, bromine, iodine, and combinations thereof. Thus, representative anions include hydroxide, acetate, sulfate, carboxylate, tetrafluoroborate, and halides such as fluoride, chloride, bromide, and iodide. Hydroxide and iodide are particularly preferred as anions.

It has also been found that when the organic templating agent comprises a mixture comprising a 3,5-DMP compound and a tetraalkylammonium ("TAA") compound, crystallization time is shortened considerably. While not wishing to be bound by any theory, it is believed that the TAA facilitates nucleation and quickly forms very small crystals (though not necessarily of SSZ-46). The 3,5-DMP templating agent then forms the pure phase SSZ-46 around the nuclei formed by the TAA. Besides speeding crystallization, use of the combination of TAA and 3,5-DMP compounds can produce smaller crystallites than when either templating agent is used alone under corresponding conditions.

Suitable TAA compounds include, but are not limited to, tetrabutylammonium and tetrapropylammonium compounds. Preferably, the TAA compound is a tetrabutylammonium compound. The anion for the TAA compounds may be selected from those described above for the 3,5-DMP) compounds.

When mixtures of 3,5-DMP and TAA compounds are used, they are generally used in a mole ratio of TAA compound(s) to 3,5-DMP compound(s) of from about 1:2 to about 1:500.

Preferably, this mole ratio is from about 1:50 to about 1:200.

A surprising advantage of using a mixture of 3,5-DMP and TAA compounds as the organic templating agent is that crystallization occurs much faster than when a 3,5-DMP compound is used alone. Thus, when only a 3,5-DMP compound is used as the organic template, crystallization of the titanium-containing zeolite typically takes about 30 days. However, when a 3,5-DMP/TAA mixture is used, crystallization typically takes only about ten days.

The Preparation of Titanium-Containing Zeolites

The process of the present invention comprises forming a reaction mixture containing sources of titanium oxide; sources an oxide of silicon, germanium or mixtures thereof (Y); an organic templating agent comprising at least one 3,5-DMP compound (Q); and water, said reaction mixture having a composition in terms of mole ratios within the following ranges:

| Reactants | General | Preferred |
|---|---|---|
| $YO_2/TiO_3$ | >25 | 30–200 |
| $OH/YO_2$ | 0.15–0.40 | 0.20–0.35 |
| $Q/YO_2$ | 0.15–0.40 | 0.20–0.35 |
| $H_2O/YO_2$ | 15–100 | 25–45 |

The reaction mixture may be prepared using standard zeolite preparation techniques. Typical sources of silicon oxide include silica hydrogel, tetraalkyl orthosilicates, and fumed silica. Typical sources of titanium include tetraalkylorthotitanates. In addition, coprecipitates comprised of both silicon and titanium can be used as a starting reagent.

Unlike the preparation of aluminosilicate zeolites, the reaction mixture for preparing the titanium-containing zeolites of this invention should not contain alkali metal hydroxide. The presence of alkali metal cations in the reaction mixture can give rise to an undesirable titanium phase in the final product. In addition, all of the hydroxide ions needed in the reaction mixture are supplied by the organic templating agent.

The titanium-containing zeolites of this invention should be free of aluminum in order to perform optimally as oxidation catalysts. It is, however, possible that traces of aluminum may be introduced into the zeolite from, e.g., a silica source which contains minor amounts of aluminum. If this occurs, the protons associated with the aluminum should be replaced with ammonium, alkali metal or alkaline earth cations.

In preparing the titanium-containing zeolites according to the present invention, the reactants and the templating agent are dissolved in water and the resulting reaction mixture is maintained at an elevated temperature until crystals are formed. The temperatures during the hydrothermal crystallization step are typically maintained from about 100° C. to about 250° C., preferably from about 140° C. to about 200° C. The crystallization period is typically greater than about five days and generally about six days to about 30 days, depending upon whether the templating agent employed is a 3,5-DMP compound alone, or a mixture of 3,5-DMP and TAA compounds. Preferably the crystallization period is from about five days to about 20 days.

The hydrothermal crystallization is usually conducted under pressure and usually in an autoclave so that the reaction mixture is subject to autogenous pressure. The reaction mixture can be stirred during crystallization.

Once the crystals have formed, the solid product is separated from the reaction mixture by standard mechanical separation techniques, such as filtration. The crystals are water-washed and then dried, e.g., at 90° C. to 150° C. for from 8 to 24 hours, to obtain the as-synthesized zeolite crystals. The drying step can be performed at atmospheric or subatmospheric pressures.

During the hydrothermal crystallization step, the crystals can be allowed to nucleate spontaneously from the reaction mixture. The reaction mixture can also be seeded with crystals of titanium-containing zeolites containing the MEL crystal structure, or with crystals of ZSM-11 crystals (which contain the MEL structure) both to direct, and accelerate the crystallization, as well as to minimize the formation of any undesired crystalline phases. When seed crystals are used, typically 0.1% to about 10%. of the weight of silica used in the reaction mixture are added.

Due to the unpredictability of the factors which control nucleation and crystallization in the art of crystalline oxide synthesis, not every combination of reagents, reactant ratios, and reaction conditions will result in crystalline products. Selecting crystallization conditions which are effective for producing crystals may require routine modifications to the reaction mixture or to the reaction conditions, such as temperature, and/or crystallization time. Making these modifications are well within the capabilities of one skilled in the art.

The titanium-containing zeolite product made by the process of this invention has an as-synthesized composition comprising, in terms of mole ratios in the anhydrous state, the following:

$$YO_2/TiO_2 > 30$$

$$Q/YO_2 \quad 0.03 - 0.10$$

The titanium-containing zeolite product was identified by its X-ray diffraction (XRD) pattern. The X-ray powder diffraction patterns were determined by standard techniques. The radiation was the K-alpha/doublet of copper. The peak heights I and the positions, as a function of 2θ where θ is the Bragg angle, were read from the relative intensities, $100 \times I/I_o$, where $I_o$ is the intensity of the strongest line or peak, and d, the interplanar spacing in Angstroms corresponding to the recorded lines, can be calculated.

The X-ray diffraction pattern of Table I is representative of as-synthesized SSZ-46 made in accordance with this invention. Minor variations in the diffraction pattern can result from variations in the silica-to-titania mole ratio of the particular sample due to changes in lattice constants. In addition, sufficiently small crystals will affect the shape and intensity of peaks, leading to significant peak broadening.

TABLE I

As-Synthesized SSZ-46

| d (Å) | Relative Intensity[a] |
|---|---|
| 14.23 | W |
| 11.14 | M |
| 10.04 | W |
| 6.70 | W |
| 5.99 | W |
| 5.57 | W |
| 5.00 | W |
| 4.60 | W |
| 4.36 | W |
| 3.84 | VS |
| 3.71 | M |
| 3.48 | W |
| 3.06 | W |
| 2.98 | W |
| 2.01 | W |

[a]The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows a typical X-ray diffraction pattern for as-synthesized SSZ-46 zeolite made in accordance with this invention. In Table IA, the intensity (I) of the peaks or lines is expressed as the intensity relative to the strongest peak or line in the pattern, i.e., $I/I_o \times 100$ where $I_o$ is the intensity of the strongest peak or line.

TABLE IA

AS-SYNTHESIZED SSZ-46

| d (Å) | $I/I_o \times 100$ |
|---|---|
| 14.23 | 1.3 |
| 11.14 | 32.6 |
| 10.04 | 16.1 |
| 6.70 | 6.1 |
| 5.99 | 9.9 |
| 5.57 | 5.4 |
| 5.00 | 6.0 |
| 4.60 | 6.2 |
| 4.36 | 6.1 |
| 3.84 | 100.0 |
| 3.71 | 27.8 |
| 3.48 | 2.6 |
| 3.06 | 9.8 |
| 2.98 | 10.9 |
| 2.01 | 9.8 |

The X-ray diffraction pattern of Table II is representative of calcined SSZ-46 made in accordance with this invention.

TABLE II

Calcined SSZ-46

| d (Å) | Relative Intensity |
|---|---|
| 14.18 | W |
| 11.14 | VS |
| 10.04 | S |
| 6.71 | W |
| 5.98 | M |
| 5.58 | W |
| 5.01 | W |
| 4.60 | W |

TABLE II-continued

Calcined SSZ-46

| d (Å) | Relative Intensity |
|---|---|
| 4.36 | W |
| 3.84 | VS |
| 3.71 | M |
| 3.49 | W |
| 3.06 | W |
| 2.99 | W |
| 2.01 | W |

Calcination can also result in changes in the intensities of the peaks as well as minor shifts in the diffraction pattern. Notwithstanding these minor perturbations, the basic crystal lattice remains unchanged by this treatment.

Table IIA below shows the X-ray diffraction pattern of calcined SSZ-46 made in accordance with this invention, including the intensities of the peaks or lines.

TABLE IIA

CALCINED SSZ-46

| | |
|---|---|
| 14.18 | 1.4 |
| 11.14 | 70.0 |
| 10.04 | 45.0 |
| 6.71 | 7.8 |
| 5.98 | 22.4 |
| 5.58 | 9.7 |
| 5.01 | 12.5 |
| 4.60 | 4.7 |
| 4.36 | 3.8 |
| 3.84 | 100.0 |
| 3.71 | 26.6 |
| 3.49 | 2.8 |
| 3.06 | 9.7 |
| 2.99 | 13.9 |
| 2.01 | 11.9 |

Pure Phase SSZ-46

The SSZ-46 of this invention is in pure phase form. As used herein, the phrase "pure phase form" refers to the fact that the SSZ-46 of this invention is composed of crystals having only the MEL crystal structure, i.e., the crystals contain no other crystal structure as an intergrowth with the MEL structure. It is believed that, heretofore, although "pure" titanium-containing zeolites containing the MEL crystal structure (i.e., TS-2) may have been reported as having been prepared, these materials have actually contained some amount of an intergrowth of another crystal structure, typically ZSM-5. One of the principal advantages of this invention is that it provides SSZ-46 without these intergrowths of other crystal structures.

It is believed that the peak in Tables I and II above found at about d=14 Å demonstrates that the SSZ-46 of this invention is in pure phase form. This peak is not found in X-ray diffraction patterns of TS-2 which contains ZSM-5 intergrowth, and does appear in Tables I and II where it would be expected in a calculated X-ray diffraction pattern for pure phase SSZ-46. In addition, the intensities of the peaks in Tables I and II above are consistent with the intensities expected for a pure phase SSZ-46. It should be noted, however, that as the amount of titanium in the SSZ-46 is increased, the peaks in the XRD pattern tend to broaden, with the result that the aforementioned peak at d=14 Å may become obscured.

Oxidation Reactions

The SSZ-46 prepared by the process of this invention is useful as a catalyst in the oxidation of hydrocarbons. Examples of such reactions include, but are not limited to, the epoxidation of olefins, oxidation of alkanes, and the oxidation of cyclohexane.

The amount of SSZ-46 catalyst employed is not critical, but should be sufficient so as to substantially accomplish the desired oxidation reaction in a practicably short period of time. The optimum quantity of catalyst will depend upon a number of factors including reaction temperature, the reactivity and concentration of the hydrocarbon substrate, hydrogen peroxide concentration, type and concentration of organic solvent, as well as the activity of the catalyst. Typically, however, the amount of catalyst will be from about 0.001 to 10 grams per mole of hydrocarbon.

Typically, the titanium-containing crystalline zeolites of this invention are thermally treated (calcined) prior to use as a catalyst.

The catalyst may be utilized in powder, pellet, microspheric, monolithic, extruded, or any other suitable physical form. The use of a binder (co-gel) or support in combination with the SSZ-46 may be advantageous. Supported or bound catalysts may be prepared by the methods known in the art to be effective for zeolite catalysts in general.

Illustrative binders and supports (which preferably are non-acidic in nature) include silica, alumina, silica-alumina, silica-titania, silica-thoria, silica-magnesia, silica-zirconia, silica-beryllia, and ternary compositions of silica with other refractory oxides. Also useful are clays such as montmorillonites, kaolins, bentonites, halloysites, dickites, nacrites and anaxites. The proportion of SSZ-46 to binder may range from about 99:1 to about 1:99, but preferably is from about 5:95 to about 80:20, all expressed on a weight basis.

The oxidizing agent employed in the oxidation processes of this invention is a hydrogen peroxide source such as hydrogen peroxide ($H_2O_2$) or a hydrogen peroxide precursor (i.e., a compound which under the oxidation reaction conditions is capable of generating or liberating hydrogen peroxide).

The amount of hydrogen peroxide relative to the amount of hydrocarbon substrate is not critical, but must be sufficient to cause oxidation of at least some of the hydrocarbon. Typically, the molar ratio of hydrogen peroxide to hydrocarbon is from about 100:1 to about 1:100, preferably 10:1 to about 1:10. When the hydrocarbon is an olefin containing more than one carbon-carbon double bond, additional hydrogen peroxide may be required. Theoretically, one equivalent of hydrogen peroxide is required to oxidize one equivalent of a mono-unsaturated substrate, but it may be desirable to employ an excess of one reactant to optimize selectivity to the epoxide. In particular, the use of a small to moderate excess (e.g., 5 to 50%) of olefin relative to hydrogen peroxide may be advantageous for certain substrates.

If desired, a solvent may additionally be present during the oxidation reaction in order to dissolve the reactants other than the SSZ-46, to provide better temperature control, or to favorably influence the oxidation rates and selectivities. The solvent, if present, may comprise from 1 to 99 weight percent of the total oxidation reaction mixture and is preferably selected such that it is a liquid at the oxidation reaction temperature. Organic compounds having boiling points at atmospheric pressure of from about 25° C. to about 300° C. are generally preferred for use. Excess hydrocarbon may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol). More than one type of solvent may be utilized. Water may also be employed as a solvent or diluent.

The reaction temperature is not critical, but should be sufficient to accomplish substantial conversion of the substrate hydrocarbon within a reasonably short period of time. It is generally advantageous to carry out the reaction to achieve as high a hydrogen peroxide conversion as possible, preferably at least about 50%, more preferably at least about 90%, most preferably at least about 95%, consistent with reasonable selectivities. The optimum reaction temperature will be influenced by catalyst activity, hydrocarbon reactivity, reactant concentrations, and type of solvent employed, among other factors, but typically will be in a range of from about 0° C. to about 150° C. (more preferably from about 25° C. to about 120° C.). Reaction or residence times from about one minute to about 48 hours (more desirably from about ten minutes to about eight hours) will typically be appropriate, depending upon the above-identified variables. Although subatmospheric pressures can be employed, the reaction is preferably performed at atmospheric or at elevated pressure (typically, between one and 100 atmospheres), especially when the boiling point of the hydrocarbon substrate is below the oxidation reaction temperature. Generally, it is desirable to pressurize the reaction vessel sufficiently to maintain the reaction components as a liquid phase mixture. Most (over 50%) of the hydrocarbon substrate should preferably be present in the liquid phase.

The oxidation process of this invention may be carried out in a batch, continuous, or semi-continuous manner using any appropriate type of reaction vessel or apparatus such as a fixed bed, transport bed, fluidized bed, stirred slurry, or CSTR reactor. The reactants may be combined all at once or sequentially. For example, the hydrogen peroxide or hydrogen peroxide precursor may be added incrementally to the reaction zone. The hydrogen peroxide could also be generated in situ within the same reactor zone where oxidation is taking place.

Once the oxidation has been carried out to the desired degree of conversion, the oxidized product may be separated and recovered from the reaction mixture using any appropriate technique such as fractional distillation, extractive distillation, liquid-liquid extraction, crystallization, or the like.

Olefin Epoxidation

One of the oxidation reactions for which SSZ-46 is useful as a catalyst is the epoxidation of olefins. The olefin substrate epoxidized in the process of this invention may be any organic compound having at least one ethylenically unsaturated functional group (i.e., a carbon-carbon double bond) and may be a cyclic, branched or straight-chain olefin. The olefin may contain aryl groups (e.g., phenyl, naphthyl). Preferably, the olefin is aliphatic in character and contains from 2 to about 30 carbon atoms. The use of light (low-boiling) $C_2$ to $C_{10}$ mono-olefins is especially advantageous.

More than one carbon-carbon double bond may be present in the olefin, i.e., dienes, trienes and other polyunsaturated substrates may be used. The double bond may be in a terminal or internal position in the olefin or may alternatively form part of a cyclic structure (as in cyclohexene, for example).

Other examples of suitable substrates include unsaturated fatty acids or fatty acid derivatives such as esters or glycerides, and oligomeric or polymeric unsaturated compounds such as polybutadiene. Benzylic and styrenic olefins may also be epoxidized, although the epoxides of certain styrenic olefins such as styrene may further react or isomerize under the conditions utilized in the present invention to form aldehydes and the like.

The olefin may contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this invention include ethylene, propylene, the butenes (i.e., 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, styrene (and other vinyl aromatic substrates), polybutadienes, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinyl cyclohexane, vinyl cyclohexene, methallyl ketone, allyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters) and the like.

Olefins which are especially useful for epoxidation are the $C_2$–$C_{30}$ olefins having the general structure

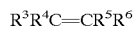

$$R^3R^4C\!=\!CR^5R^6$$

wherein $R^3$, $R^4$, $R^5$ and $R^6$ are the same or different and are selected from the group consisting of hydrogen and $C_1$–$C_{20}$ alkyl.

Mixtures of olefins may be epoxidized and the resulting mixtures of epoxides either employed in the mixed form or separated into the different component epoxides.

The following examples demonstrate but do not limit the present invention.

EXAMPLES

There are numerous variations on the embodiments of the present invention illustrated in the Examples which are possible in light of the teachings supporting the present invention. It is therefore understood that within the scope of the following claims, the invention may be practiced otherwise than as specifically described or exemplified.

Example 1

Preparation of 3,5-dimethyl-N,N-diethylpiperidinium hydroxide templating agent (Template A)

200 Grams of 3,5-dimethylpiperidine, 255 grams of potassium bicarbonate and 1700 ml of methanol were added to a 3-liter 3-necked flask which was equipped with a mechanical stirrer, addition funnel and reflux condenser. 794 Grams of ethyl iodide was added to the resulting reaction mixture and, once addition was complete, the mixture was heated for three days at reflux. After cooling, the reaction mixture was concentrated and the desired solids isolated. The product, 3,5-dimethyl-N,N-diethylpiperidinium iodide, was recrystallized from hot acetone/methanol.

Ion exchange to the corresponding hydroxide was achieved using Bio-Rad AG1-X8 anion exchange resin. The hydroxide ion concentration was determined by titration of the resulting solution using phenolphthalein as the indicator.

Example 2

Synthesis of SSZ-46

9.22 Grams of a 15.46 weight percent 3,5-dimethyl-N,N-diethylpiperidinium hydroxide (Template A) solution were added to a beaker equipped with a stir bar. 0.0628 Gram of tetraethylorthotitanate (TEOT) was then added to the beaker under rigorous stirring. To the resulting clear solution was added 3.63 grams of water. Finally, 1.53 grams of fumed, amorphous silica (CabOSil M-5) was added slowly under stirring and blended until a homogeneous mixture was obtained. A small amount of seed crystals (0.007 gram of pure phase ZSM-11 made with Template A) was added to speed crystallization. All reactants should be free from inorganic alkali. The resulting gel had a molar ratio as follows:

Si:Ti:Template A:H$_2$O=1:0.01:0.3:25

The gel was charged into a 20 ml capacity Teflon-lined autoclave and tumbled (43 RPM) at 175° C. under autogenous pressure for two weeks. The resulting crystalline product was recovered by filtration, and readied for catalysis by calcination in air at 595° C. for five hours.

The crystalline product of this reaction was determined by X-ray diffraction (XRD) to be a titanium-containing zeolite having the MEL crystal structure in pure phase form, i.e., SSZ-46, having the following characteristic X-ray diffraction lines:

TABLE III

| d (Å) | I/I$_o$ × 100 |
|---|---|
| 14.17 | 1.0 |
| 11.13 | 27.7 |
| 10.03 | 19.7 |
| 7.45 | 10.2 |
| 6.69 | 5.5 |
| 5.98 | 9.8 |
| 5.57 | 5.0 |
| 5.01 | 4.9 |
| 4.60 | 5.3 |
| 4.35 | 5.8 |
| 3.84 | 100.0 |
| 3.71 | 28.1 |
| 3.48 | 3.2 |
| 3.06 | 9.5 |
| 2.98 | 11.4 |
| 2.01 | 9.2 |

Example 3

Synthesis of SSZ-46

6.6 Grams of a 11.36 weight percent solution of Template A was combined with 5.68 grams of water and stirred until homogeneous. The final reactant mixture was prepared by adding 0.96 gram of a silica-titania coprecipitate (Si/Ti mole ratio=54), such as W. R. Grace Si-Ti. Type III/2. The resulting mixture had a molar ratio as follows:

Si:Ti:Template A:H$_2$O=1:19:0.25:40

After adding 0.01 gram of pure phase ZSM-11 crystals (made with Template A) as seed crystals, the entire mixture was placed in a 20 ml capacity Teflon-lined autoclave and tumbled (43 RPM) at 175° C. under autogenous pressure for two weeks. The resulting crystalline product was recovered by filtration and readied for catalysis by calcination in air at 595° for five hours.

The crystalline product was analyzed by XRD and found to be SSZ-46 having the following characteristic X-ray diffraction lines:

TABLE IV

| d (Å) | I/I$_o$ × 100 |
|---|---|
| 11.16 | 44.6 |
| 10.06 | 21.2 |
| 7.46 | 14.0 |
| 6.70 | 8.8 |
| 6.00 | 11.4 |
| 5.57 | 7.3 |
| 5.02 | 4.8 |
| 4.61 | 6.9 |
| 4.36 | 9.4 |
| 3.85 | 100.0 |
| 3.71 | 38.8 |
| 3.48 | 3.1 |
| 3.06 | 8.8 |
| 2.98 | 12.2 |
| 2.01 | 9.0 |

Example 4

Synthesis of SSZ-46

25 Grams of tetraorthosilicate (TEOS) was placed in a round bottom flask fitted with a stir bar, and 0.865 gram of TEOT was added thereto followed by dropwise addition of 69.1 grams of a 11.37 weight percent solution of Template A. The mixture was kept in an ice bath during the addition of the Template A. After all of the Template A had been added, the ice bath was removed and the mixture allowed to stir at room temperature for five hours. The flask was then heated to 60° C. under vacuum to accelerate hydrolysis and evaporate the ethyl alcohol which is released. After all the alcohol had been removed, water was added so that the final gel composition had the following molar ratio:

Si:Ti:Template A:H$_2$O=1:0.03:0.35:28

A small amount of seed crystals (0.04 gram of pure phase ZSM-11 made with Template A) was added to the resulting clear colorless solution, which was then transferred into Teflon-lined autoclaves and tumbled at 160° C. under autogenous pressure for four weeks. The resulting crystalline product was recovered by centrifugation and readied for catalysis by calcination in air at 595° C. for five hours.

The crystalline product was determined by XRD to be SSZ-46 having the following characteristic X-ray diffraction lines:

TABLE V

| d (Å) | I/I$_o$ × 100 |
|---|---|
| 11.15 | 46.8 |
| 10.05 | 24.0 |
| 7.45 | 11.5 |

TABLE V-continued

| d (Å) | I/I$_o$ × 100 |
|---|---|
| 6.69 | 6.9 |
| 6.00 | 10.7 |
| 5.57 | 5.9 |
| 5.01 | 4.2 |
| 4.60 | 6.7 |
| 4.36 | 8.9 |
| 3.84 | 100.0 |
| 3.71 | 36.1 |
| 3.06 | 7.1 |
| 2.98 | 10.7 |
| 2.01 | 8.1 |

Example 5

Synthesis of SSZ-46

The procedure described in Example 3 was used, except that the reaction mixture contained 13.19 grams TEOS, 0.15 gram TEOT, and 25.53 grams of an 11.36 wt % aqueous solution of Template A. This resulted in the following molar composition:

Si:Ti:Template A: H$_2$O=1:0.01:0.25:40

The resulting clear, colorless solution was placed in Teflon-lined autoclaves and a small amount of seed crystals (0.075 gram of a pure phase ZSM-11 made using Template A) was added to speed crystallization. The autoclaves were tumbled at 175° C. under autogenous pressure for 12 days. The resulting crystalline product was recovered by filtration and readied for catalysis by calcination in air at 595° C. for 5 hours.

The crystalline product was determined by XRD to be SSZ-46.

Example 6

Synthesis of SSZ-46

13.9 Grams of TEOS was placed in a round bottom flask fitted with a stir bar, and 0.232 gram of TEOT was added followed by dropwise addition of 26.3 grams of an 11.36 wt % solution of Template A. The mixture was kept in an ice bath during the addition of the TEOT. After all of the TEOT had been added, the ice bath was removed and the mixture allowed to stir at room temperature for 5 hours. Then, 0.16 gram of an aqueous solution of tetrabutylammonium hydroxide (55%) was added to the flask. The flask was then heated to 60° C. under vacuum to accelerate hydrolysis and evaporate the ethyl alcohol which was released. After all of the alcohol had been removed, water was added so that the final gel composition, on a molar basis, was as follows:

Si:Ti:Template A:H$_2$O=1:0.015:0.245:0.005:40

The resulting clear, colorless solution was then transferred into Teflon-lined autoclaves and tumbled at 175° C. under autogenous pressure for 8 days. The resulting crystalline product was recovered by filtration and readied for catalysis by calcination in air at 595° C. for 5 hours.

The crystalline product was determined by XRD to be SSZ-46.

Example 7

Epoxidation of 1-Octene

Fifty mg of each in turn of the powdered catalysts indicated in Table A below, 6 ml of acetone, 10 millimoles of 1-octene, 0.1 gram of mesitylene (as internal standard), and 3.3 millimoles of aqueous H$_2$O$_2$ (31.1% w/w) were loaded into a glass autoclave equipped with a magnetic stir bar. The autoclave was then immersed into a constant temperature oil bath maintained at 60° C. The reactants were allowed to stir vigorously for 3 hours at this temperature.

After this time, the solution was allowed to return to ambient temperature and the residual amount of H$_2$O$_2$ was determined by cerimetric titration. The reaction product was analyzed by quantitative gas chromatography to determine the conversion of 1-octene. The results are indicated in Table A below.

TABLE A

| Catalyst | 1-Octene Conversion (%) | H$_2$O$_2$ Effciency (%) |
|---|---|---|
| TS-2 | 9.62 | 73.9 |
| Ex. 2 | 9.27 | 86.3 |
| Ex. 3 | 6.38 | 97.2 |
| Ex. 6 | 8.47 | 85.0 |

Example 8

Oxidation of n-Octane

Fifty mg of each in turn of the powdered catalysts indicated in Table B below, 6 ml of acetone, 30 millimoles of n-octane, 0.3 gram of mesitylene (as internal standard), and 10 millimoles of aqueous H$_2$O$_2$ (31.1% w/w) were loaded into a glass autoclave equipped with a magnetic stir bar. The autoclave was then immersed into a constant temperature oil bath maintained at 100° C. The reactants were allowed to stir vigorously for 4 hours at this temperature.

After this time, the solution was allowed to return to ambient temperature and the residual amount of H$_2$O$_2$ was determined by cerimetric titration. The reaction product was analyzed by quantitative gas chromatography to determine the conversion of n-octane. The results are indicated in Table B below.

TABLE B

| Catalyst | n-Octane Conversion (%) |
|---|---|
| Ex. 2 | 21.7 |
| Ex. 6 | 16.0 |

What is claimed is:

1. A crystalline composition containing MEL crystal structure, as-synthesized and in the anhydrous state, whose general formula, in terms of mole ratios, is YO$_2$/TiO$_2$  > 30

Q/YO$_2$  0.03 – 0.1 wherein Q is an organic templating agent comprising at least one 3,5-dimethylpiperidinium compound, and Y comprises silicon, germanium, or mixtures thereof.

2. The crystalline composition of claim 1 having no intergrowth within its crystalline structure of any crystal structure other than MEL.

3. A process for preparing titanium-containing zeolites containing MEL crystal structure which comprises:

(a) preparing an aqueous solution containing (1) sources of titanium oxide; (2) sources of an oxide selected from oxides of silicon, germanium or mixtures thereof; and
(3) an organic templating agent comprising at least one 3,5-dimethylpiperidinium compound;
(b) maintaining the aqueous solution under conditions sufficient to form crystals of said titanium-containing zeolite; and
(c) recovering the crystals of said titanium-containing zeolite.

4. A process according to claim 3 wherein said templating agent has the general formula:

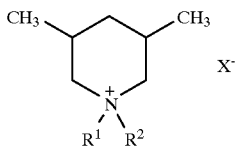

wherein $R^1$ and $R^2$ independently represent an alkyl group, either branched or unbranched, substituted or unsubstituted, containing from 1 to about 7 carbon atoms, with the proviso that $R^1$ and $R^2$ are not both methyl, or $R^1$ and $R^2$ together comprise a cyclic alkyl ring system, which, including the positively charged nitrogen atom, contains from 4 to 7 atoms, said ring system being unsubstituted or substituted with branched or unbranched alkyl groups, and $X^-$ is an anion which is not detrimental to the formation of the titanium-containing zeolite.

5. A process according to claim 4 wherein X is hydroxide.

6. The process of claim 3 wherein the 3,5-dimethylpiperidinium compound is a 3,5-dimethyl-N,N-diethylpiperidinium compound.

7. The process of claim 3 wherein the 3,5-dimethylpiperidinium compound is a 1-azonia-3,5,7-trimethyl-spiro[5.4]decane compound.

8. The process of claim 3 wherein the 3,5-dimethylpiperidinium compound is a 3,5-dimethyl-N-methyl-N-ethylpiperidinium compound.

9. The process of claim 3 wherein the organic templating agent comprises a mixture of a 3,5-dimethylpiperidinium compound and a tetraalkylammonium compound.

10. The process of claim 3 wherein the titanium-containing zeolite is in pure phase form.

* * * * *